(12) United States Patent
Petukhov

(10) Patent No.: US 9,108,943 B2
(45) Date of Patent: Aug. 18, 2015

(54) PHOTOREACTIVE BENZAMIDE PROBES FOR HISTONE DEACETYLASE 2

(71) Applicant: THE BOARD OF TRUSTEES OF THE UNIVERSITY OF ILLINOIS, Urbana, IL (US)

(72) Inventor: Pavel Petukhov, Chicago, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 14/308,094

(22) Filed: Jun. 18, 2014

(65) Prior Publication Data

US 2014/0371469 A1   Dec. 18, 2014

Related U.S. Application Data

(60) Provisional application No. 61/836,389, filed on Jun. 18, 2013.

(51) Int. Cl.
*C07D 333/24* (2006.01)
*C07C 247/16* (2006.01)
*C07C 247/18* (2006.01)

(52) U.S. Cl.
CPC ............ *C07D 333/24* (2013.01); *C07C 247/16* (2013.01); *C07C 247/18* (2013.01)

(58) Field of Classification Search
CPC .................................................... C07D 333/24

USPC ......................................................... 549/77
See application file for complete search history.

(56) References Cited

PUBLICATIONS

Bressi et al., Bioorg. Med. Chem. Lett. 2010, 20, 3142.
Butler et al., J. Am. Chem. Soc. 2010, 132, 10842.
Chou et al., J. Biol. Chem. 2008, 283, 35402.
Cravatt, J. Am. Chem. Soc. 2008, 130, 2184.
Dowling et al., Biochemistry 2010, 49, 5048.
Hosoya et al., Org. Biomol. Chem. 2004, 2, 637.
Jones et al., J. Mol. Biol. 1997, 267, 727.
Methot et al., Bioorg. Med. Chem. Lett. 2008, 18, 973.
Neelarapu et al., J. Med. Chem. 2011, 54, 4350.
Somoza et al., Structure 2004, 12, 1325.
Suzuki, Clin. Cancer Res. 2009, 15, 3163.
Umezawa et al., Bioorg. Med. Chem. 2010, 18, 6340.
Vaidya et al., "Design, synthesis, modeling, biological evaluation and photoaffinity labeling studies of novel series of photoreactive benzamide probes for histone deacetylase 2," Bioorganic & Medical Chemistry Letters, 2012, 22:5025-5030.
Verdonk et al., Proteins 2003, 52, 609.
Watson et al., Nature 2012, 481, 335.
Witter et al., Bioorg. Med. Chem. Lett. 2008, 18, 726.

*Primary Examiner* — Taofiq A Solola
(74) *Attorney, Agent, or Firm* — Michael Best & Friedrich LLP

(57) ABSTRACT

The design, modeling, synthesis, biological evaluation, and photoaffinity labeling studies of a series of photoreactive potent and selective HDACs 1 and 2 benzamide based probes are disclosed herein.

13 Claims, 6 Drawing Sheets

FIGURE 1

Table 1. Potency of the probes against class I HDAC isoforms

| # | HDAC1 IC$_{50}$(nM) | | | HDAC2 IC$_{50}$(nM) | | | HDAC3 %Inhibition(10μM) | | HDAC8 %Inhibition(10μM) | |
|---|---|---|---|---|---|---|---|---|---|---|
| | Preincubation time | | | Preincubation time | | | Preincubation time | | Preincubation time | |
| | 5 min | 3 h | 5 min | 3 h | 24 h | 5 min | 3 h | 5 min | 3 h |
| 1a | 2100 ± 44 | 140 ± 34 | 5130 ± 470 | 1050 ± 81 | 210 ± 17 | 6.6 | 35 | NA | NA |
| 1b | 1200 ± 85 | 70 ± 5.3 | 3200 ± 260 | 690 ± 57 | 110 ± 36 | 8.7 | 56 | NA | 4.7 |
| 1c | 5600 ± 520 | 1400 ± 160 | 18000 ± 910 | 5200 ± 400 | 2400 ± 74 | 2.2 | 27 | NA | 11 |
| 1d | 21000 ± 100 | 13000 ± 320 | 32000 ± 1700 | 21000 ± 720 | 10000 ± 490 | NA | 24 | NA | 14 |
| 1e | 23000 ± 1400 | 2700 ± 69 | 34000 ± 2300 | 6500 ± 120 | 830 ± 28 | 4.3 | 16 | NA | 22 |
| 1f | 18000 ± 130 | 3800 ± 54 | 17000 ± 4400 | 6600 ± 140 | 750 ± 81 | 7.6 | 12 | NA | 6.6 |
| 1g | 96000 ± 1600 | 55000 ± 1300 | 120000 ± 4900 | 94000 ± 530 | 77000 ± 4100 | 2.0 | 6.5 | NA | 26 |
| 2a | 3800 ± 120 | 780 ± 22 | 3800 ± 540 | 1000 ± 70 | 320 ± 32 | 7.8 | 48 | NA | 25 |
| 2b | 2500 ± 280 | 990 ± 53 | 7000 ± 250 | 1100 ± 25 | 350 ± 16 | 11 | 46 | NA | 22 |
| 2c | 2800 ± 240 | 1210 ± 68 | 7100 ± 220 | 1800 ± 50 | 300 ± 77 | 21 | 47 | NA | 24 |
| 1 | 410 ± 16 | 52 ± 4.3 | 1200 ± 93 | 350 ± 15 | 140 ± 6 | 26 | 96 | NA | 3.0 |
| 2 | 14500 ± 1300 | 1880 ± 5.2 | 38000 ± 2000 | 14000 ± 1030 | 740 ± 49 | 8.8 | 40 | NA | 3.0 |
| SAHA | 29 ± 1.6 | 34 ± 3.2 | 200 ± 14 | ND | 260 ± 4.3 | 100 | 100 | 100 | 100 |

NA – no inhibition up to 10μM concentration, ND – not determined. Data are mean ± SD of three independent experiments.

FIGURE 2

Table 2
Ratios of IC50 for HDACs 1, 2 and 3 with respect to preincubation time and selectivity for HDAC1 vs 2. ND - not determined

| # | HDAC1 IC$_{50}$ ratio 3 h/5 min | HDAC2 IC$_{50}$ ratio 3 h/5 min | HDAC2 IC$_{50}$ ratio 24 h/5 min | HDAC3 %inhibition ratio 3 h/5 min | HDAC2/HDAC1 IC$_{50}$ ratio 3 h/3 h | HDAC2/HDAC1 IC$_{50}$ ratio 24 h/3 h |
|---|---|---|---|---|---|---|
| 1a | 1.5 | 4.9 | 24 | 5.3 | 7.5 | 1.5 |
| 1b | 1.7 | 4.6 | 29 | 6.4 | 9.9 | 1.6 |
| 1c | 4.0 | 3.5 | 7.5 | 12 | 3.7 | 1.7 |
| 1d | 1.6 | 1.5 | 3.2 | - | 1.6 | 0.77 |
| 1e | 8.5 | 5.2 | 41 | 3.7 | 2.4 | 0.31 |
| 1f | 4.7 | 2.6 | 23 | 1.6 | 1.7 | 0.20 |
| 1g | 1.7 | 1.3 | 1.6 | 3.3 | 1.7 | 1.4 |
| 2a | 4.9 | 3.8 | 12 | 6.2 | 1.3 | 0.41 |
| 2b | 2.5 | 6.4 | 20 | 4.2 | 1.1 | 0.35 |
| 2c | 2.3 | 7.1 | 24 | 2.2 | 0.82 | 0.25 |
| 1 | 7.9 | 3.4 | 8.6 | ND | 6.7 | 2.7 |
| 2 | 7.8 | 2.7 | 52 | 4.5 | 7.5 | 0.39 |
| SAHA | 0.85 | ND | 0.77 | 1.0 | ND | 7.7 |

PHOTOREACTIVE BENZAMIDE PROBES FOR HISTONE DEACETYLASE 2

CROSS REFERENCE TO RELATED APPLICATION

This application claims priority to U.S. Provisional Patent Application No. 61/836,389, filed on Jun. 18, 2013, the entire contents of which are hereby incorporated by reference.

STATEMENT REGARDING FEDERALLY SPONSORED RESEARCH

This invention was made with United States government support awarded by the National Institutes of Health, Grant No. R01CA131970. The United States Government has certain rights in this invention.

BACKGROUND

Histone deacetylases (HDACs) are considered viable drug targets for therapeutic applications including cancer and neurological disorders.

SUMMARY

In one aspect, the disclosure provides a compound of formula (I):

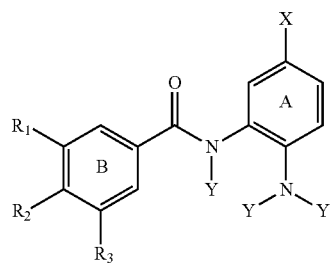

or a salt, hydrate or solvate thereof, wherein:

X is selected from the group consisting of azido, aryl, substituted aryl, heteroaryl and substituted heteroaryl;

each Y is independently selected from the group consisting of hydrogen, alkyl and substituted alkyl;

$R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl; and rings A and B are optionally further substituted with one or more substituents selected from the group consisting of halo, alkyl, alkoxy, aryl and acyl.

In another aspect, the disclosure provides a compound of formula (II):

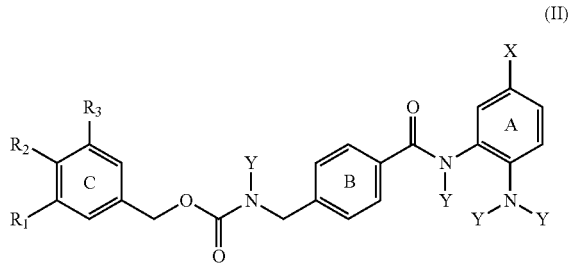

or a salt, hydrate or solvate thereof, wherein:

X is selected from the group consisting of azido, aryl, substituted aryl, heteroaryl and substituted heteroaryl;

each Y is independently selected from the group consisting of hydrogen, alkyl and substituted alkyl;

$R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl; and rings A and B are optionally further substituted with one or more substituents selected from the group consisting of halo, alkyl, alkoxy, aryl and acyl.

Other aspects and embodiments of the disclosure will become apparent in light of the following description and drawings.

BRIEF DESCRIPTION OF THE DRAWINGS

FIG. 1 shows a table, Table 1, including data demonstrating the potency of certain compounds described herein against class I HDAC isoforms.

FIG. 2 shows a table, Table 2, including ratios of the IC50s for HDACs 1, 2 and 3 with respect to preincubation time and selectivity for HDAC1 vs 2. (ND—not determined).

DETAILED DESCRIPTION

Figure 3:
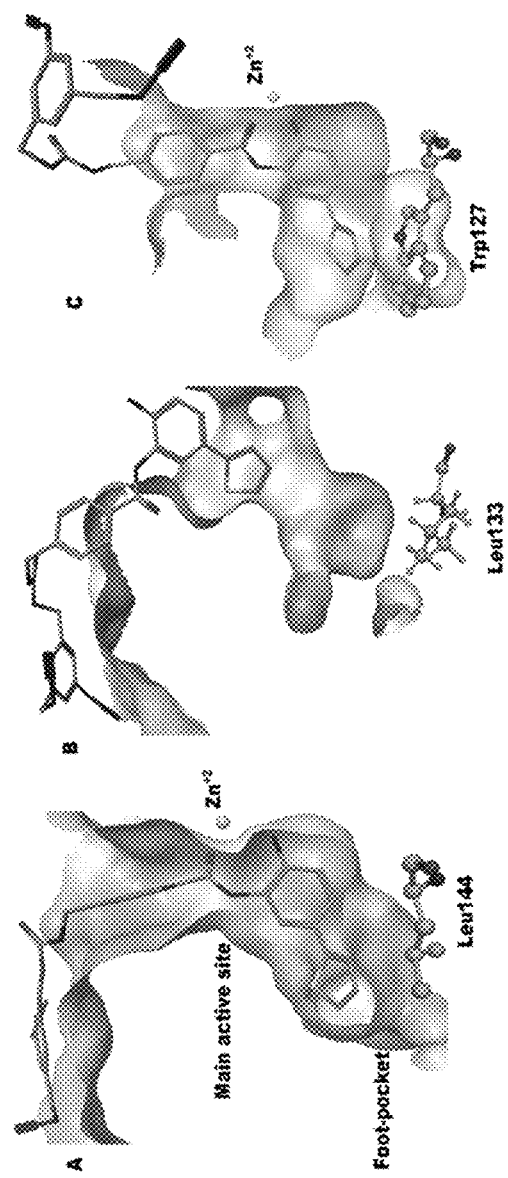
FIG. 3 shows models of probe 2c docked into the active site of: (A) HDAC2, (B) HDAC3, and (C) HDAC8.

The inventors have successfully designed and synthesized highly potent and selective probes for HDAC3 and HDAC8 and demonstrated that they are cell permeable and exhibit excellent antiproliferative activity against several cancer cell lines.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkoxy" refers to an —O-alkyl radical.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group, or a $C_1$-$C_4$ alkyl group. Examples of $C_1$-$C_4$ alkyl groups include methyl, ethyl, n-propyl, isopropyl, n-butyl, sec-butyl, iso-butyl and tert-butyl groups. An alkyl group may be unsubstituted or may be substituted, e.g., with one or more substituents.

The term "alkylenyl" refers to a divalent alkyl group, examples of which include but are not limited to —CH$_2$—, —CH$_2$CH$_2$—, —CH$_2$CH$_2$CH$_2$— and —CH$_2$CH(CH$_3$)CH$_2$—. An alkylenyl group may be optionally substituted with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "azide" or "azido" refers to a group of the formula —N$_3$.

The term "azidoalkyl" refers to an alkyl group as described herein, substituted with an azido group. Non-limiting examples of azidoalkyl groups include —CH$_2$N$_3$ and —CH$_2$CH$_2$N$_3$.

The term "azidoalkoxy" refers to an alkoxy group as described herein, substituted with an azido group. Non-limiting examples of azidoalkoxy groups include —OCH$_2$N$_3$ and —O—CH$_2$CH$_2$N$_3$.

The term "azidoalkylamidyl" refers to a group of the formula —NHC(O)-alkylenyl-N$_3$. Non-limiting examples of azidoalkylamidyl groups include —NHC(O)CH$_2$N$_3$ and —NHC(O)CH$_2$CH$_2$N$_3$.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "substituents" refers to a group "substituted" on an alkyl, alkenyl, alkynyl, cycloalkyl, cycloalkylalkyl, heterocyclyl, heterocyclylalkyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C═O), phosphonate, sulfinyl, sulfonyl, sulfonate, sulfonamino, sulfonamido, thioamido, thiol, thioxo (e.g., C═S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, Ph, Ac and Ts represent methyl, ethyl, phenyl, acetyl and tosyl (p-toluenesulfonyl), respectively. A more comprehensive list of the abbreviations used by organic chemists of ordinary skill in the art appears in the first issue of each volume of the Journal of Organic Chemistry, and/or in the guidelines for authors of the same journal; this list is typically presented in a table entitled Standard Abbreviations and Acronyms. The abbreviations contained in said list, and all abbreviations used by organic chemists of ordinary skill in the art, are hereby incorporated by reference.

Where chemical substituents or groups are specified by their conventional chemical formulae, written from left to right, they optionally encompass substituents or groups resulting from writing the structure from right to left, e.g., —$CH_2NH$— optionally also recites —$NHCH_2$—. While certain lists of substituent groups include a group shown in both orientations, it should be expressly understood that any substituent group written in a certain direction (e.g., left to right) also encompasses the same group in the other direction (e.g., right to left).

"Treat" or "treating" as used herein refers to administering a regimen to the subject, e.g., the administration a compound or composition described herein, such that the disorder or at least one symptom of the disorder is healed, alleviated, relieved, altered, remedied, ameliorated, and/or improved. Treating includes administering an amount effective to alleviate, relieve, alter, remedy, ameliorate, improve and/or affect the disorder or the symptoms of the disorder. The treatment may inhibit deterioration or worsening of a symptom of a disorder.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

Compounds described herein may serve as probes for histone deacetylases (HDACs), for example, HDAC1 and HDAC2. The compounds may alternately be referred to as "compounds" and "probes" herein.

Compounds disclosed herein include compounds of formula (I):

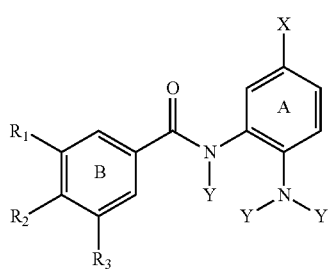

(I)

or a salt, hydrate or solvate thereof, wherein:
X is selected from the group consisting of azido, aryl, substituted aryl, heteroaryl and substituted heteroaryl;
each Y is independently selected from the group consisting of hydrogen, alkyl and substituted alkyl;
$R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl; and
rings A and B are optionally further substituted with one or more substituents selected from the group consisting of halo, alkyl, alkoxy, aryl and acyl.

In some embodiments, one of $R_1$, $R_2$ and $R_3$ is selected from the group consisting of azido, azidoalkyl, azidoalkoxy, and azidoalkylamidyl. In some embodiments, two of $R_1$, $R_2$ and $R_3$ are selected from the group consisting of azido, azidoalkyl, azidoalkoxy, and azidoalkylamidyl. In some embodiments, $R_1$ is selected from the group consisting of hydrogen and azido. In some embodiments, $R_2$ is selected from the group consisting of hydrogen, azido, azidoalkoxy (e.g., —$OCH_2CH_2N_3$), and azidoalkylamidyl (e.g., —NHC(O)$CH_2CH_2N_3$). In some embodiments, $R_3$ is selected from the group consisting of hydrogen and azidoalkyl (e.g., —$CH_2N_3$). In some embodiments, $R_1$ is hydrogen, $R_2$ is azido, and $R_3$ is hydrogen. In some embodiments, $R_1$ is azido, $R_2$ is hydrogen, and $R_3$ is azidoalkyl (e.g., —$CH_2N_3$). In some embodiments, $R_1$ is azido, $R_2$ is azidoalkoxy (e.g., —$OCH_2CH_2N_3$), and $R_3$ is hydrogen. In some embodiments, $R_1$ is hydrogen, $R_2$ is azidoalkylamidyl (e.g., —NHC(O)$CH_2CH_2N_3$), and $R_3$ is hydrogen. In some embodiments, each Y is hydrogen. In some embodiments, X is selected from the group consisting of azido, aryl (e.g., phenyl) and heteroaryl (e.g., thiophenyl).

In some embodiments, the compound of formula (I) is selected from the group consisting of:
N-(4-amino-[1,1'-biphenyl]-3-yl)-4-azidobenzamide;
N-(2-amino-5-(thiophen-2-yl)phenyl)-4-azidobenzamide;
N-(2-amino-5-(thiophen-2-yl)phenyl)-3-azido-5-(azidomethyl)benzamide;
N-(4-amino-[1,1'-biphenyl]-3-yl)-3-azido-5-(azidomethyl)benzamide;
N-(4-amino-[1,1'-biphenyl]-3-yl)-3-azido-4-(2-azidoethoxy)benzamide;
N-(2-amino-5-(thiophen-2-yl)phenyl)-3-azido-4-(2-azidoethoxy)benzamide; and
N-(2-amino-5-azidophenyl)-4-(3-azidopropanamido)benzamide.

Compounds disclosed herein also include compounds of formula (II):

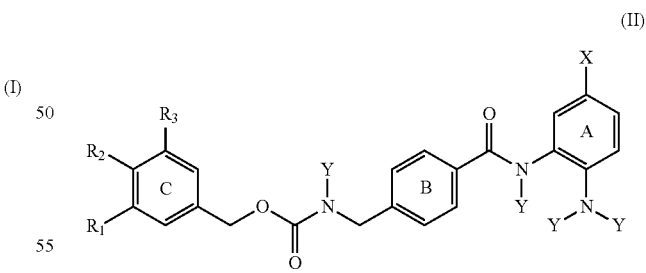

(II)

or a salt, hydrate or solvate thereof, wherein:
X is selected from the group consisting of azido, aryl, substituted aryl, heteroaryl and substituted heteroaryl;
each Y is independently selected from the group consisting of hydrogen, alkyl and substituted alkyl;
$R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl; and rings A and B are optionally further substituted with one or more substituents selected from the group consisting of halo, alkyl, alkoxy, aryl and acyl.

In some embodiments, one of $R_1$, $R_2$ and $R_3$ is selected from the group consisting of azido, azidoalkyl, azidoalkoxy, and azidoalkylamidyl. In some embodiments, two of $R_1$, $R_2$ and $R_3$ are selected from the group consisting of azido, azidoalkyl, azidoalkoxy, and azidoalkylamidyl. In some embodiments, one of $R_1$, $R_2$ and $R_3$ is selected from the group consisting of azido and alkylazido. In some embodiments, two of $R_1$, $R_2$ and $R_3$ are selected from the group consisting of azido and alkylazido. In some embodiments, $R_1$ is selected from the group consisting of hydrogen and azido. In some embodiments, $R_2$ is selected from the group consisting of hydrogen, azido, azidoalkoxy (e.g., —OCH$_2$CH$_2$N$_3$), and azidoalkylamidyl (e.g., —NHC(O)CH$_2$CH$_2$N$_3$). In some embodiments, $R_3$ is selected from the group consisting of hydrogen and azidoalkyl (e.g., —CH$_2$N$_3$). In some embodiments, $R_1$ is azido, $R_2$ is hydrogen, and $R_3$ is hydrogen. In some embodiments, $R_1$ is azido, $R_2$ is hydrogen, and $R_3$ is azidoalkyl (e.g., —CH$_2$N$_3$). In some embodiments, each Y is hydrogen. In some embodiments, X is selected from the group consisting of aryl (e.g., phenyl) and heteroaryl (e.g., thiophenyl).

In some embodiments, the compound of formula (II) is selected from the group consisting of:
3-azidobenzyl 4-((4-amino-[1,1'-biphenyl]-3-yl)carbamoyl)benzylcarbamate;
3-azido-5-(azidomethyl)benzyl 4-((4-amino-[1,1'-biphenyl]-3-yl)carbamoyl)benzylcarbamate; and
3-azido-5-(azidomethyl)benzyl 4-((2-amino-5-(thiophen-2-yl)phenyl)carbamoyl)benzylcarbamate.

Compounds of formula (I) and (II) can be prepared according to a variety of methods, including but not limited to those illustrated in the Examples. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

Isomers

Compounds described herein (e.g., compounds of formula (I), (Ia), (Ib), (II), (III) and (IV)) may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Salts

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N-0<<).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$)

Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

2. COMPOSITIONS AND ROUTES OF ADMINISTRATION

In another aspect, the disclosure may provide pharmaceutical compositions comprising one or more compounds of this disclosure (e.g., a compound of formula (I) or formula (II)) in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective $GABA_A$ receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

3. METHODS OF USE

Compounds described herein, such as compounds of formula (I) or formula (II), may serve as probes for histone deacetylases (HDACs), for example, HDAC1 and HDAC2. In such embodiments, they may be used in methods of inhibiting a histone deacetylase, such as HDAC1 or HDAC2. They may also be used to photocrosslink HDACs, and for mapping HDAC binding sites.

Compounds described herein, such as compounds of formula (I) or formula (II), may be used in a method of treating a neurological disorder, or in a method of treating a proliferative disorder such as cancer.

The present disclosure has multiple aspects, illustrated by the following non-limiting examples.

4. EXAMPLES

Example 1

Compound Synthesis

Scheme 1. Amine and acid precursors used for synthesis.

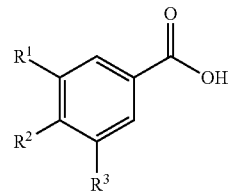

3, $R^1 = H$, $R^2 = N_3$, $R^3 = H$
4, $R^1 = N_3$, $R^2 = H$, $R^3 = CH_2N_3$
5, $R^1 = N_3$, $R^2 = -O(CH_2)_2N_3$, $H$, $R^3 = H$
6, $R^1 = H$, $R^2 = NHCO(CH_2)_2N_3$, $R^3 = H$

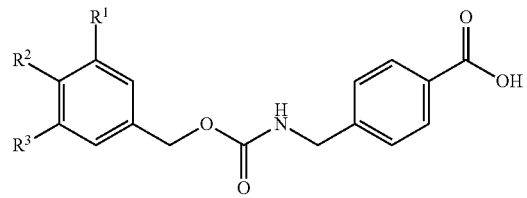

7, $R^1 = N_3$, $R^2 = H$, $R^3 = H$
8, $R^1 = N_3$, $R^2 = H$, $R^3 = CH_2N_3$

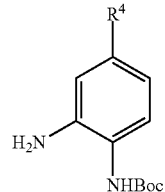

9, $R^4 = Ph$
10, $R^4 = $ 2-thiophenyl
11, $R^4 = N_3$

Scheme 2. Synthesis

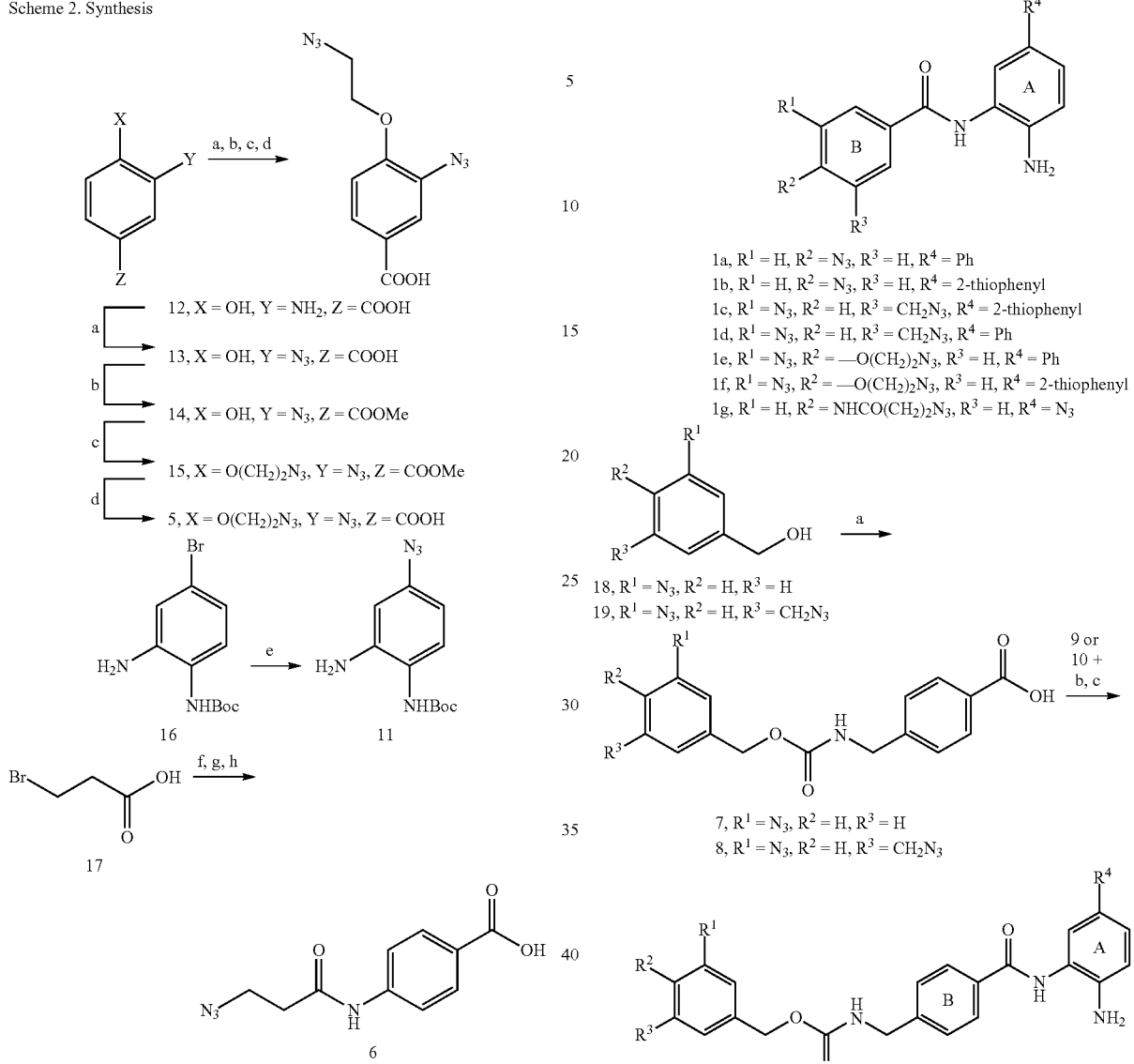

Reagents and conditions used in Scheme 2: a NaNO$_2$, HCl, NaN$_3$, 5 h, 0° C. - rt, 85%; b SOCl$_2$, MeOH, 8 h, 0° C. - rt, 87%; c K$_2$CO$_3$, 2-azidoethyl-4-methylbenzene sulphonate, acetone, 5 h, reflux, 77%; d THF/H$_2$O (1:1), KOH, 10 h, 70° C., 92%; e NaN$_3$, Sod. ascorbate, CuI, N,N-dimethylethane-1,2-diamine, EtOH/H$_2$O, reflux, 92%; f i: NaN$_3$, CH$_3$CN, reflux, 80%; ii: oxalyl chloride, DCM, 6 h; g methyl 4-aminobenzoate, Pyridine, DCM, 0° C. - rt, 86%; h 2 N NaOH, THF/H$_2$O (8:2), 2 h, rt, 93%.

Scheme 3. Synthesis

Reagents and conditions used in Scheme 3: a CDI, DBU, TEA, 4-(aminomethyl)benzoic acid, THF, 10 h, 0° C. - rt, 90-92%; b EDCI, HOBt, DMF, 12 h, 80° C., 80-90%; c TFA/DCM, 0.5 h, rt, 90-95%.

Substituted benzoic acids 3-8, mono-N-Boc protected phenylenediamines 9, 10 and azidoaniline 11 shown in FIG. 2 were chosen as precursors for the synthesis of the photoreactive probes. Acid 4, protected phenylendiamines 9, 10, and intermediates 16, 18 and 19 were synthesized as reported previously. Hosoya et al. *Org. Biomol. Chem.* 2004, 2, 637; Neelarapu et al. *J. Med. Chem.* 2011, 54, 4350; Witter et al. *Bioorg. Med. Chem. Lett.* 2008, 18, 726; Umezawa et al. *Bioorg. Med. Chem.* 2010, 18, 6340. Benzoic acid 3 was available commercially. The synthesis of precursors 5, 6, 7, 8, and 11 is shown in Schemes 2 and 3. The synthesis of the probes 1a-g and 2a-b proceeded through an efficient carbodiimide based coupling reaction between mono-N-Boc protected phenylendiamines 9-11 and benzoic acids 3-8 followed by deprotection of the resulting N-Boc products to give the final probes in 70-80% overall yield (Scheme 3).

General procedure for synthesis: To a solution of substituted benzoic acid 3-8 (1.1 equiv) in anhydrous DMF (5 mL/mmol of amine) was added EDCI (1.2 equiv) followed by HOBt (1.2 equiv) and stirred at room temperature for 1 h. Thereafter protected phenylendiamine 9-11 (1 equiv) was added and the mixture heated at 78° C. overnight. After completion of the reaction as confirmed by TLC, saturated sodium bicarbonate solution (20 mL/mmoL of amine) was added and the mixture was extracted with ethylacetate (30 mL/mmol of amine) The organic layer was washed with water (30 mL/mmol of amine), dried over anhydrous sodium sulphate and evaporated in vacuo. The residue was purified using flash chromatography (silica gel, hexane/ethylacetate gradient) to yield the N-boc protected probes. The Boc group was subsequently removed by treating N-boc protected compound with a mixture of TFA/DCM (1:1 v/v) at room temperature for 1 h. The solvent was removed in vacuo and the residue purified using flash chromatography (silica gel, hexane/ethylacetate gradient) to yield the final probes as solids in 70-80% over all yield. Spectral data for probe 1b; 1H NMR (400 MHz, DMSO-d6) δ (ppm) 9.83 (bs, 1H), 8.05 (d, J=8.4 Hz, 2H), 7.40-7.25 (m, 6H), 7.06-7.04 (m, 1H), 6.86 (d, J=8.4 Hz, 1H). 13 C NMR (100 MHz, DMSO-d6) δ (ppm). 164.13, 144.42, 143.13, 142.33, 131.33, 130.28, 128.75, 124.49, 124.44, 124.36, 123.96, 123.60, 121.80, 119.36, 117.48. $(M+H)^+$ 336.40. Spectral data for probe 2c; 1H NMR (400 MHz, DMSO-d6) δ (ppm) 9.79 (bs, 1H), 8.00-7.95 (m, 2H), 7.65-7.55 (m, 3H), 7.52-7.35 (m, 4H), 7.33-7.23 (m, 1H), 7.18 (s, 1H), 7.09 (s, 1H), 6.89 (d, J=8.4 Hz, 1H), 5.08 (s, 2H), 4.49 (s, 2H) 4.29 (s, 2H). 13 C NMR (100 MHz, DMSO-d6) δ (ppm) 165.39, 156.32, 143.35, 140.15, 140.05 140.01, 138.18 138.16, 133.17, 128.89 (2C), 128.74 (2C), 127.95 (2C), 126.81 (2C), 126.19, 125.61, 124.78, 123.91, 118.24, 117.61, 116.95, 64.46, 52.96, 43.68. $(M+H)^+$541.60.

Example 2

Inhibitory Profiles

The inhibitory profile of the probes against class I HDAC isoforms was determined using a fluorogenic assay and the results are given in Table 1 shown in FIG. 1. The inhibition of HDAC8 was measured using the fluorogenic acetylated substrate Fluor de Lys and purified recombinant human HDAC8 from *E. coli* (Dowling et al. *Biochemistry* 2010, 49, 5048) whereas the inhibition of HDAC1-3 was measured using fluorogenic acetylated substrate Boc-L-Lys(Ac)-AMC and commercially available recombinant human HDAC1-3.

HDAC inhibition assay was performed in 96-well opaque half-area microplate (Corning). Human recombinant HDAC1, 2 and 3 (BPS Bioscience) and HDAC8 (partially purified from *E. Coli*) were diluted with assay buffer 1 (25 mM Tris-HCl, pH 8.0, 137 mM NaCl, 2.7 mM KCl, 1 mM MgCl2, and 1 mg/mL BSA), so as to have 4 ng/μl, 5 ng/μl and 1 ng/μl and 8.5 ng/μL stocks of each isoform respectively. Serial dilutions of the probes were made in assay buffer 2 (25 mM Tris-HCl, pH 8.0, 137 mM NaCl, 2.7 mM KCl, 1 mM MgCl2). 10 μL of the enzyme stock was added to 30 μL of the probes and preincubated for different preincubation times. It was observed the Z-factor for the assays remained above 0.7 up to 3 h for HDAC1, 3 and 8 and up to 24 h for HDAC2, hence these preincubation times were chosen for the assays. After preincubation, 10 μL of 125 μM HDAC fluorescent substrate Boc-L-Lys (Ac)-AMC (Chem-Impex) in case of HDAC1, 2 and 3 and 10 μL of 25 μM BML-KI-178 (Biomol Inc.) in case of HDAC8 was added, and the mixture incubated for 35 min (HDAC1, 3, 8), 60 min (HDAC2) at room temperature. The reaction was quenched with 50 μL of 1 mg/mL trypsin and 5 μM trichostatin A in assay buffer 1 (25 mM Tris-HCl, pH 8.0, 137 mM NaCl, 2.7 mM KCl, 1 mM MgCl2) and further incubated at room temperature for 35 min. The plate was read on Synergy 4 hybrid microplate reader (Bio-Teck) at excitation wavelength 360 nm and emission wavelength 460 nm. The IC50 values were determined using the GraphPad Prism 5 software (GraphPad Software Inc., La Jolla, Calif.)

The effect of preincubation with HDAC1, 2, 3, and 8 was also explored, as it was previously observed that the potency of the benzamide-based HDAC inhibitors increased with preincubation with HDAC1-3 (Bressi et al. *Bioorg. Med. Chem. Lett.* 2010, 20, 3142; Chou et al. *J. Biol. Chem.* 2008, 283, 35402). The maximum incubation time was chosen on the basis of stability of HDAC proteins in the conditions used to determine $IC_{50}$ values. For HDAC1, 3, and 8 the maximum incubation time was 3 hours, whereas HDAC2 protein was stable for 24 hours. The $IC_{50}$ values of ligands 1 and 2 determined in this study vary from those reported previously (Witter et al. *Bioorg. Med. Chem. Lett.* 2008, 18, 726; Bressi et al. *Bioorg. Med. Chem. Lett.* 2010, 20, 3142). This discrepancy may be attributed to the differences in the assay conditions, the protein sources, substrates, and preincubation times. The analysis of SAR was facilitated by docking all the probes to HDAC2, (PDB:3MAX) (Bressi et al. *Bioorg. Med. Chem. Lett.* 2010, 20, 3142), HDAC3 (PDB:4A69) (Watson et al. *Nature* 2012, 481, 335), and HDAC8 (PDB: 1T69) (Somoza et al. *Structure* 2004, 12, 1325) using GOLD v.5.1 (Jones et al. *J. Mol. Biol.* 1997, 267, 727; Verdonk et al. *Proteins* 2003, 52, 609).

All the newly synthesized benzamide-based probes had activity ranging between 70 nM and 55 μM and 110 nM and 77 μM for HDAC1 and HDAC2, respectively. All of the probes demonstrated a robust 2-40-fold increase in inhibition of HDAC1 and 2 upon preincubation with the enzymes for 3 h and 24 h, respectively (Table 2 shown in FIG. 2). Consistent with the previously reported observation (Bressi et al. *Bioorg. Med. Chem. Lett.* 2010, 20, 3142), SAHA, a hydroxamate-based inhibitor, did not exhibit time-dependent inhibition. Similar trends were observed with HDAC3 and HDAC8. In the discussion below only $IC_{50}$'s obtained at the maximum preincubation time will be used, unless specified otherwise.

In general, the probes exhibited better activity and selectivity for HDAC1 and 2 as compared to HDAC3 and HDAC8 (Table 1). The most HDAC1 and 2 potent probe 1b had an estimated 100- and 1000-fold selectivity for HDAC1 and 2 as compared to HDAC3 and HDAC8, respectively. In the case of HDAC8, no inhibition was observed after 5 min, whereas inhibition of HDAC3 varied from 2% for 1g to 21% for 2c at 10 μM concentration of the inhibitors. After preincubation for 3 h, inhibition of HDAC3 and HDAC8 by the probes varied from 6.5% for 1g to 56% for 1b and from 4.7% for 1b to 26% for 1g, respectively. Similarly to the probes, ligand 1 showed pronounced inhibition of HDAC3 and HDAC8, 96% and 24%, respectively, and ligand 2 inhibited 40% of activity of HDAC3 and only 3% of activity of HDAC8. Despite the similarity of probes 2a-c, 2a did not inhibit HDAC8 at 10 μM, whereas both 2b and 2c inhibited 25% and 22% of activity of HDAC8, respectively.

Figure 4:
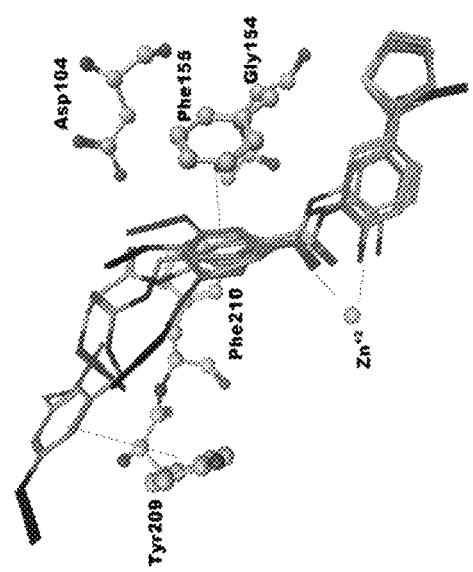
FIG. 4 shows an overlay of compounds 1b (green), 1c (magenta), 1g (cyan) and 2c (gold) in the active site of HDAC2.

Bressi et al. (*Bioorg. Med. Chem. Lett.* 2010, 20, 3142) suggested that the time-dependent inhibition in the case of HDAC2 may be explained by the gradual disruption of the internal hydrogen bond between the aniline hydrogen and carbonyl oxygen in the unbound form of the ligand so as to form a bidentate complex with $Zn^{2+}$ ion in the bound form. After a preincubation 3 h, increase in inhibition of HDAC1 and HDAC2 by the probes varied from 1.6-fold for 1d to 17-fold for 1b and from 1.3-fold for 1g to 7.1-fold for 2c respectively (Table 2). After preincubation for 24 h, inhibition of HDAC2 further improved to 1.6-fold for 1g to 41-fold for 1e. A comparison of the $IC_{50}$ ratios for 3 h vs 5 min and 24 h vs 5 min for HDAC2 (Table 2) shows that the weakest inhibitors 1c, 1d, and 1g exhibit the least pronounced change in their $IC_{50}$ with time. A somewhat similar but less pronounced trend is observed in the case of HDAC1. In general, the trends observed in our case seem to be consistent with the explanation for the time-dependent inhibition given by Bressi et al. The difference in the time-dependent inhibition by the probes that have the same substituent binding to the "foot pocket", e.g. 1a, 1c, 1e, 2a, and 2b, at 3 h vs 5 min and 24 h vs 5 min suggests that additional factors should be taken into account. Overall ability of the ligands to adopt the necessary conformation for induced fit may play a role in addition to the conformational flexibility of the benzamide portion of the ligands. HDAC1 is highly homologous to HDAC2, and, therefore, its time-dependent inhibition may be explained in a similar fashion. However, neither HDAC3 nor HDAC8 were reported to have crystal structures that would contain a binding pocket similar to the "foot pocket" of HDAC2. The docking of the probes to HDAC2 showed that their binding poses are essentially the same as that of ligand 1, i.e. the aniline nitrogen and the amide oxygen form a bi-dentate chelate with $Zn^{2+}$, whereas the bi-aryl portion occupies the "foot pocket" (FIGS. 3 and 4).

Example 3

Docking Poses

A comparison of the docking pose of probe 2c in HDAC2, HDAC3, and HDAC8 shows that, unlike HDAC2 (FIG. 3A), HDAC3 (FIG. 3B) and HDAC8 (FIG. 3C) cannot accommodate 2c such that it can form a bi-dentate complex with $Zn^{2+}$ in the catalytic site. The binding site of HDAC3 in 4A69 is too small for 2c and the probe is mostly resides outside the binding site. In HDAC8 in 1T69, the binding site is too short and has a somewhat different shape compared to HDAC2. None of the docking poses of 2c coordinates with $Zn^{2+}$ despite the proximity of the groups necessary for coordination. After a co-minimization of 2c with the HDAC8, only coordination between the carbonyl oxygen of 2c and $Zn^{2+}$ was observed. Interestingly, although the residues in the foot pocket of HDAC2 and the corresponding residues in HDAC3 (according to sequence alignment) are the same, the recent X-ray apo-structure of HDAC3[17] did not contain a "foot pocket". Watson et al. (*Nature* 2012, 481, 335) noted that the HDAC3 structure was crystallized in the absence of the ligand and, therefore, may not be representative of the actual protein-ligand complex interactions. In our opinion, the similarity of the time-dependent inhibition of HDAC2 and HDAC3 and HDAC8 suggests that the latter two isoforms may also adopt the conformation with a "foot pocket" that can accommodate the benzamide-based ligands. The relatively low inhibition of HDAC8 compared to HDAC1-3 may be rationalized by the difference in the residues at the entrance to the "foot-pocket" that imposes different steric and electrostatic requirements on the $R^4$ substituent. In HDAC8, the opening to the putative "foot pocket" is hindered by the presence of bulky sidechain of Trp127 as shown in FIG. 3, whereas in HDAC1, 2 and 3 the corresponding residue Leu144 is less bulky and more flexible and makes the "foot pocket" more accessible to the ligands.

This is also indirectly supported by the SAR—probe 1g is consistently the least active against HDAC1-3 but its inhibition of HDAC8 is comparable to that of 1, 1e, 2b, and 2c.

Salisbury and Cravatt (*J. Am. Chem. Soc.* 2008, 130, 2184) attributed the low potency of benzophenone based benzamide probes to the positioning of the photoreactive group. Based on those observations, a small SAR study was carried out to explore how the positioning of the aryl azide and aliphatic azide affects the potency and selectivity of the probes. Despite the presence of additional azido groups, probes 1a and 1b were comparable in potency to ligand 1 and probes 2a-c were more than 2-2.5-fold more potent than ligand 2 for HDAC1 and 2. Probes 1c-g were 27-1000 and 5-550-fold less potent than ligand 1 for HDAC1 and 2 respectively. In general, probes 1a-g were found to be less potent than ligand 1 for both HDAC3 and 8, whereas compounds 2a-c and ligand 2 demonstrated comparable potency against HDAC3. In HDAC8, the diazide probes 2b and 2c appear to be more potent than ligand 2 and the monoazide probe 2a was inactive. To gain insights into the plausible explanations for the difference in potency, the docking poses of the probes were compared with that of ligand 1. The meta-substituents $R^1$ and $R^3$ are too close to the residues Phe210, Gly154, Phe155, Leu276, and Asp104 (FIG. 4).

As a result of this steric interference, the probes are forced to adopt a conformation where the face-to-face π-π stacking between ring B of the probes and Phe155 is disrupted. The loss of these π-π stacking interactions may explain relatively poor potency of mono meta-substituted probes 1e and 1f, 830 and 750 nM respectively, and especially 3,5-disubstituted probes 1c and 1d, 2.4 μM and 10 μM respectively, compared to probes with no meta substituents 1a and 1b, 210 and 110 nM, respectively. The width and shape of the gorge region appears to be important to gain potency and isoform selectivity as demonstrated by Butler et al. (*J. Am. Chem. Soc.* 2010, 132, 10842) in design of tubastatin A, a selective inhibitor of HDAC6. Placement of the aromatic azido group in the "foot-pocket" in 1g led to poor potency for HDAC1 and 2, 55 μM and 77 μM respectively, slightly less pronounced decrease in inhibition of HDAC3 but not HDAC8. The docking showed that the $R^4$ azido substituent fits well in the "foot pocket" and occupies the same space as the $R^4$ phenyl and 2-thiophenyl substituents in 1a-f. This observation appears to be consistent with the SAR found by Methot et al. (*Bioorg. Med. Chem. Lett.* 2008, 18, 973) where non-polar aromatic substituents were found to be preferable compared to polar and/or relatively small substituents $R^4$. The additional interactions between the carbamate appendage in probes 2a, 2b and 2c and Tyr209 of HDAC2 identified by docking did not contribute to potency of these ligands, suggesting that this appendage is likely to remain solvent exposed.

Example 4

Crosslinking Studies

Figure 5:
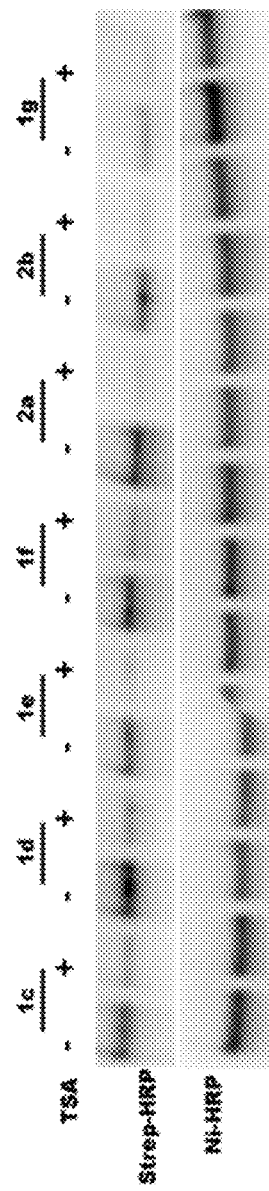
FIG. 5 shows a representative Western blot of three independent experiments, demonstrating the characterization of biotinylated HDAC2 and His-tagged HDAC2 using streptavidin-HRP and nickel-HRP. Western blot analysis of diazide probes 1c, 1d, 1e, 1f, 2b, 2c and 1g (25 µM) photocrosslinked to HDAC 2 (1.25 µM) in the presence or absence of 125 µM of Trichostatin A (TSA) using streptavidin-HRP and nickel-HRP.

Photoaffinity labeling studies were conducted with the probes using commercially available recombinant His-tagged HDAC2. The probes (25 μM) were preincubated with HDAC2 (1.25 μM) for 24 h in photolabeling buffer, exposed to 254 nm UV light for 3×1 min with 1 min resting. A commercially available strained cyclooctyne based biotin tag (BT) was attached to the HDAC2-probe adduct using (3+2) cycloaddition reaction and the biotinylated HDAC2 was visualized by streptavidin-HRP and western blot analysis (FIG. 5). The loading was confirmed by using nickel-HRP, which recognized the His-tag of the recombinant HDAC2 protein.

Diazide probe (25 µM) or probe-TSA (25 µM-probe and 125 µM-TSA) mixture was incubated with HDAC2 (1.25 µM) for 24 h in photolabelling buffer (25 mM Tris-HCl, pH 8.0, 137 mM NaCl, 2.7 mM KCl, 1 mM MgCl2, 0.1% Triton-X), exposed to 254 nm UV light 3×1 min with 1 min resting. 500 µM of DBCO-PEG4-biotin conjugate (Click Chemistry tools) in photolabeling buffer was added to initiate the [3+2] cycloaddition reaction with HDAC2-probe adduct. The cycloaddition reaction was carried out for 3 h at room temperature. Western blotting was done with 1.5 ug of purified protein with 5× loading buffer containing 10% SDS, 0.05% bromophenol blue, 50% glycerol, and β-mercaptoethanol. Protein samples were boiled for 5 mM and allowed to cool before loading on a denaturing 4-15% polyacrylamide gel electrophoresis (SDS PAGE). After electrophoresis, protein was transferred to a polyvinylidiene difluoride membrane (Iblot-Invitrogen). The membrane was incubated for 12 h with 5% albumin fraction V (Sigma-aldrich) in 1× Tris based saline supplemented with 0.1% Tween-20 (TBS-T). The membrane was washed three times with TBST and then incubated with Ni-HRP (1:2000) in TBST for 1 h under room temperature with slight agitation. After three washes in TBS-T, the chemilumiscent signal was detected using the enhanced chemiluminescence (ECL) kit from Pierce (Pierce Biotechnology, Rockford, Ill.). The membrane was washed three times with 1× phosphate buffer saline supplemented 0.1% Tween-20 (PBS-T), and stripped of Ni-HRP by incubating with 5% BSA, 2M Imidazole in PBST for 1 h at room temperature. After three washes of PBST, the membrane was incubated with Streptavidin-HRP (1:5000) in PBST for 1 h. After three washes in PBST and water, the chemilumiscent signal was detected using the enhanced chemiluminescence (ECL) kit from Pierce (Pierce Biotechnology, Rockford, Ill.).

To ensure that the biotinylation was primarily driven through interactions of the probes with the binding site of HDAC2, competition experiments of the probes were performed with a known potent HDAC inhibitor Trichostatin A (125 µM), which has an $IC_{50}$ of 68 nM for HDAC2.[8] All of the diazide probes showed a pronounced decrease in biotinylation in the presence of 5-fold molar excess of the competing ligand. The decrease was slightly less pronounced in the case of weakly potent probe 1g.

Example 5

Cell Permeability and Inhibition of Nuclear HDACs

Probes 1a-f and 2a-c are cell permeable and capable of inhibiting nuclear HDACs by monitoring the acetylation status of histone H4 in MDA-MB-231 breast cancer cell line using previously published procedure. H4 is a known nuclear target for HDAC1 and HDAC2 in this cell line (Suzuki I. *Clin. Cancer Res.* 2009, 15, 3163).

DA-MB-231 cells seeded at $1.0 \times 10^5$ cells/well in 6-plates and grown to 90% confluence in DMEM (Gibco) supplemented with 10% FBS (Gibco) and 1% penicillin-streptomycin (Mediatech). Cells were treated with either DMSO or benzamide probes at a final concentration of 50 µM and maintained at 37° C. and 5% $CO_2$ for 24 h. Cells were lysed using 1×RIPA buffer (150 mM NaCl, 1% Triton X-100, 0.5% sodium deoxycholate, 0.1% SDS, 50 mM Tris, pH 8.0) containing protease inhibitor cocktail (Roche) and 1:100 dilution of phosphatase inhibitor (Sigma) with shearing. Lysates were clarified through centrifugation at 13,000 rpm at 4° C. Total protein concentration was determined via the BCA Protein Assay Kit (Pierce). Lysates were stored at −20° C. until later use. Sample vials were prepared by aliquoting 25 µg of total protein and adding 5× Sample Buffer. Sample vials were boiled for 5 min, cooled to RT, and proteins separated by gel electrophoresis at 80V. Proteins in the gel were transferred to PVDF membrane in 4 min using the Invitrogen iBlot system. Membranes were blocked using 5% Milk in PBST and probed using anti-GAPDH (1:5000) or anti-acetyl histone H4 (1:1000) overnight at 4° C. Membranes were incubated with either anti-mouse (1:5000) or anti-rabbit (1:5000) in 5% Milk in PBST. Results were visualized using Femto chemiluminescent substrate (Pierce) in CCD camera.

Figure 6:
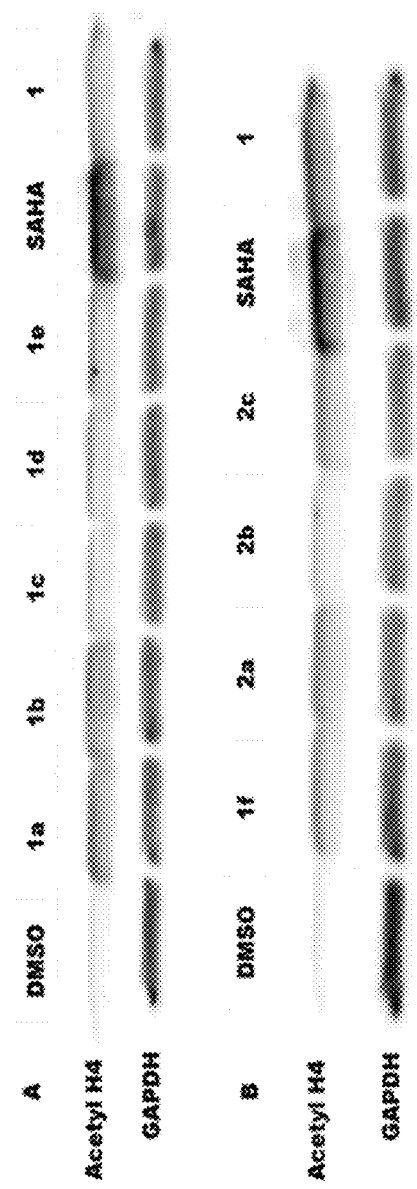
FIG. 6 shows a representative Western blot of three independent experiments, demonstrating detection of acetyl H4 in MDA-MB-231 cell lines following a 24 h treatment with probes at 50 µM. (A) Treatment of cells with probes 1a, 1b, 1c, 1d, 1e, suberoyl anilide hydroxamic acid (SAHA) and parent ligand 1. (B) Treatment of cells with probes 1f, 2a, 2b, 2c, suberoyl anilide hydroxamic acid (SAHA) and parent ligand 1.

All of the probes inhibited deacetylation of histone H4 at 50 µM concentration after a 24 h treatment (FIGS. 6A and B).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A compound of formula (I):

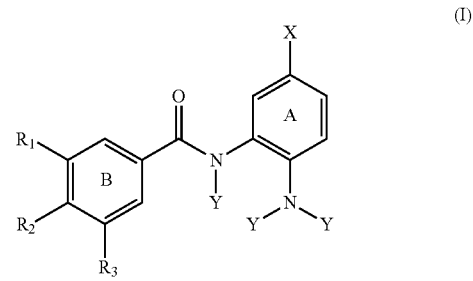

or a salt, hydrate or solvate thereof, wherein:
X is selected from the group consisting of azido, phenyl and thiophenyl;
each Y is independently selected from the group consisting of hydrogen, alkyl and substituted alkyl; and
$R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl.

2. The compound of claim 1, wherein one or two of $R_1$, $R_2$ and $R_3$ is selected from the group consisting of azido, azidoalkyl, azidoalkoxy, and azidoalkylamidyl.

3. The compound of claim 1, wherein $R_1$ is selected from the group consisting of hydrogen and azido.

4. The compound of claim 1, wherein $R_2$ is selected from the group consisting of hydrogen, azido, azidoalkoxy, and azidoalkylamidyl.

5. The compound of claim 1, wherein $R_3$ is selected from the group consisting of hydrogen and azidoalkyl.

6. The compound of claim 1, wherein each Y is hydrogen.

7. The compound of claim 1, wherein the compound is selected from the group consisting of:
N-(4-amino-[1,1'-biphenyl]-3-yl)-4-azidobenzamide;
N-(2-amino-5-(thiophen-2-yl)phenyl)-4-azidobenzamide;
N-(2-amino-5-(thiophen-2-yl)phenyl)-3-azido-5-(azidomethyl)benzamide;

N-(4-amino-[1,1'-biphenyl]-3-yl)-3-azido-5-(azidomethyl)benzamide;

N-(4-amino-[1,1'-biphenyl]-3-yl)-3-azido-4-(2-azidoethoxyl)benzamide;

N-(2-amino-5-(thiophen-2-yl)phenyl)-3-azido-4-(2-azidoethoxyl)benzamide; and

N-(2-amino-5-azidophenyl)-4-(3-azidopropanamido)benzamide.

8. A compound of formula (II):

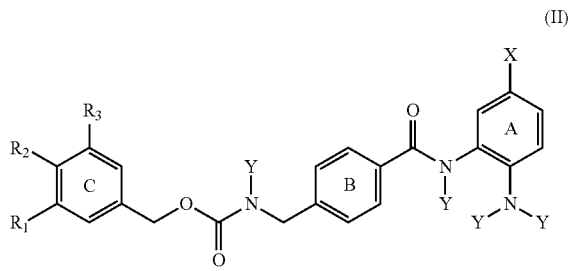

(II)

or a salt, hydrate or solvate thereof, wherein:

X is selected from the group consisting of phenyl and thiophenyl;

each Y is independently selected from the group consisting of hydrogen, alkyl and substituted alkyl; and $R_1$, $R_2$ and $R_3$ are independently selected from the group consisting of hydrogen, azido, azidoalkyl, azidoalkoxy, and azidoalkylamidyl, wherein at least one of $R_1$, $R_2$ and $R_3$ is selected from the group consisting of azido, azidoalkyl, azidoalkoxy, and azidoalkylamidyl.

9. The compound of claim 8, wherein $R_1$ is selected from the group consisting of hydrogen and azido.

10. The compound of claim 8, wherein $R_2$ is hydrogen.

11. The compound of claim 8, wherein $R_3$ is selected from the group consisting of hydrogen and azidoalkyl.

12. The compound of claim 8, wherein each Y is hydrogen.

13. The compound of claim 8, wherein the compound is selected from the group consisting of:

3-azidobenzyl 4-((4-amino-[1,1'-biphenyl]-3-yl)carbamoyl)benzylcarbamate;

3-azido-5-(azidomethyl)benzyl 4-((4-amino-[1,1'-biphenyl]-3-yl)carbamoyl)benzylcarbamate; and 3-azido-5-(azidomethyl)benzyl 4-((2-amino-5-(thiophen-2-yl)phenyl)carbamoyl)benzylcarbamate.

* * * * *